United States Patent
Spector

[11] Patent Number: 5,851,442
[45] Date of Patent: Dec. 22, 1998

[54] BUTTON-ACTUATED AIR FRESHENER

[76] Inventor: Donald Spector, 380 Mountain Rd., Union City, N.J. 07080

[21] Appl. No.: 876,190

[22] Filed: Jun. 13, 1997

[51] Int. Cl.$^6$ .................................................. B01D 47/00
[52] U.S. Cl. .............................. 261/30; 261/32; 261/104; 261/DIG. 17; 261/DIG. 65
[58] Field of Search ............................... 261/83, 84, 100, 261/102, 105, DIG. 65, 30, 33, 32, 104; 422/123, 124; 239/53, 55, 57

[56] References Cited

U.S. PATENT DOCUMENTS

| 1,080,432 | 12/1913 | Freestone | 239/54 |
| 1,285,101 | 11/1918 | Foster, Jr. | 422/124 |

FOREIGN PATENT DOCUMENTS

| 61-86926 | 5/1986 | Japan | 422/124 |

Primary Examiner—Jay H. Woo
Assistant Examiner—Robert Hopkins
Attorney, Agent, or Firm—Michael Ebert

[57] ABSTRACT

A button-actuated air freshener in which rotatable within a dome having a vented cylindrical shell is a turret having a central shaft aligned with the axis of the shell and an array of wings radiating from the shaft, each formed by a panel of porous material impregnated with a fragrance oil. Mounted on top of the dome is a spring-biased button operatively coupled to the shaft whereby when the button is depressed, this action causes the turret to spin to create within the shell an air vortex. This vortex acts to volatilize fragrance oil on the surface of the wings to produce an aromatic vapor that is discharged through vents in the shell into the atmosphere of the enclosure in which the air freshener is installed, the aromatic vapor serving to mask unpleasant odors permeating the atmosphere.

10 Claims, 2 Drawing Sheets

BUTTON-ACTUATED AIR FRESHENER

BACKGROUND OF THE INVENTION

1. Field of Invention

This invention relates generally to air fresheners, and more particularly to a button-actuated air freshener which is activated only when the button is depressed to cause the air freshener to discharge into the atmosphere of the enclosure in which the air freshener is installed, an aromatic vapor in a volume and at a rate sufficient to mask whatever unpleasant odors permeate this atmosphere.

2. Status of Prior Art

When the atmosphere of a kitchen, bathroom or other enclosure is permeated with unpleasant odors, these can be masked by discharging into this atmosphere an aromatic vapor whose volume intensity and rate are sufficient to overcome these unpleasant odors.

It is known for this purpose to use a potpourri, a mixture of herbs and spices blended with essential oils, placed in a bowl or basket. A potpourri is passive in the sense that the volume of fragrance and the rate at which it is emitted into the atmosphere depends on the prevailing ambient temperature and humidity in the room in which it is installed. Hence if the atmosphere of the room is cold and humid, relatively little fragrance will be emitted by the potpourri.

A potpourri is less effective in freshening the atmosphere of a large enclosure, and in any event it cannot do so for more than a relatively brief period before it is exhausted. However, one can revive a potpourri by tossing its ingredients in a fragrance oil.

To provide an "active" air freshener, there is disclosed in the 1991 Spector patent 5,007,529 a "Microwave Heatable Air Freshener Package". This package consists of a vented plastic container permeable to microwave energy in which is stored a foam plastic pad impregnated with a liquid fragrance.

When the package is placed within a microwave oven and is irradiated therein, the liquid fragrance is heated by the microwave energy, causing it to volatilize to generate an aromatic vapor. When the container is taken out of the oven and placed in an enclosure whose atmosphere is to be freshened, an aromatic vapor is discharged into the atmosphere through a vent in the container.

An obvious drawback of a microwave-activated air freshener is that it requires a microwave oven to operate, and in many cases this oven is not available. A more serious drawback is that the period in which the air freshener is effective is limited by the fact that once the air freshener package is removed from the microwave oven, no heat is thereafter supplied thereto, and continued vaporization depends on the residual heat retained within the package by its thermally-insulated container.

Since in an air freshener in accordance with the invention, use is made of a porous material impregnated with fragrance oil, the nature of this fragrance oil must be understood.

The aroma of perfumes and of perfume-based products, such as colognes and toilet waters, was originally derived from the essential oils of plants. Chemists later succeeded in analyzing many essential oils and in creating synthetic oils which not only simulate the fragrances of many essential oils, but also yield altogether new scents which do not exist in nature. Modern perfumes are largely blends of natural and synthetic scents and include fixatives which equalize vaporization and enhance pungency. In many liquid scents the ingredients are combined with a highly volatile alcohol carrier.

However, a porous pad impregnated with a fragrance oil of the type disclosed in the Spector patent, if not activated in a microwave oven, will only slowly release an aromatic vapor into the atmosphere, and will not serve therefore to freshen the atmosphere of a kitchen or other room having an unpleasant odor.

To understand the limitations of a fragrance oil impregnated porous material, one must take into account the process by which a substance in a liquid state is converted into a vapor. The molecules of a substance in a condensed state are held to one another by strong forces of attraction. These are balanced by equally strong repulsive forces. Tending to overcome the potential energy of attraction is the escaping tendency of molecules, which arises from their kinetic energy. The kinetic energy, and therefore the escaping tendency of molecules, is a function of temperature.

The rate of evaporation of a liquid is therefore affected by the following factors:

A. the rate at which heat is supplied to the liquid to furnish the latent heat of vaporization;

B. the rate at which the liquid is stirred to bring to the surface molecules having sufficient kinetic energy to escape; and C. the rate at which the vapor above the liquid is changed to provide optimum conditions for the escape of molecules from the surface of the liquid.

Obviously, a wet surface exposed to a high wind will experience far greater evaporation than when the air above the surface is static. In an air freshener in accordance with the invention, the heat supplied to the fragrance oil impregnating the porous panel is ambient heat at room temperature. Hence this heat alone will not promote rapid volatilization of the fragrance oil. In an air freshener in accordance with the invention operating at room temperature, rapid volatilization is promoted by an air vortex in which air impinging on the surface of porous wings impregnated with fragrance oil acts to stir this oil to bring it to the surface and to draw aromatic vapor away from the surface of the wings.

SUMMARY OF INVENTION

In view of the foregoing, the main object of this invention is to provide an air freshener which is rendered active to discharge an aromatic vapor into the atmosphere of an enclosure, simply by pressing an actuator button which causes a turret within the air freshener to spin and thereby create an air vortex.

A significant feature of a manually-operated air freshener in accordance with the invention is that it exploits the ambient heat in the room in which it is placed, and does not require the use of a microwave oven or other means to supply heat thereto.

More particularly, an object of this invention is to provide an air freshener having an array of wings formed of porous material impregnated with a fragrance oil whereby the air freshener has a large fragrance oil capacity and a prolonged operating life.

A salient advantage of an air freshener in accordance with the invention is that it is normally passive and is render active only when an operator depresses its button which he may do as many times as it takes to suffuse the enclosure in which the air freshener is installed with an aromatic vapor serving to mask whatever unpleasant odors permeate the atmosphere.

Briefly stated, these objects are attained by a button-actuated air freshener in which rotatable within a dome having a vented cylindrical shell is a turret having a central shaft aligned with the axis of the shell and an array of wings radiating from the shaft, each formed by a panel of porous material impregnated with a fragrance oil.

Mounted on top of the dome is a spring-biased button operatively coupled to the shaft whereby when the button is depressed, this action causes the turret to spin to create within the shell an air vortex. This vortex acts to volatilize fragrance oil on the surface of the wings to produce an aromatic vapor that is discharged through vents in the shell into the atmosphere of the enclosure in which the air freshener is installed, the aromatic vapor serving to mask unpleasant odors permeating the atmosphere.

BRIEF DESCRIPTION OF DRAWING

For a better understanding of the invention as well as other objects and further features thereof, reference is made to the following detailed description to be read in conjunction with the accompanying drawings, wherein.

DESCRIPTION OF INVENTION

Structure of Air Freshener

Figure 1:
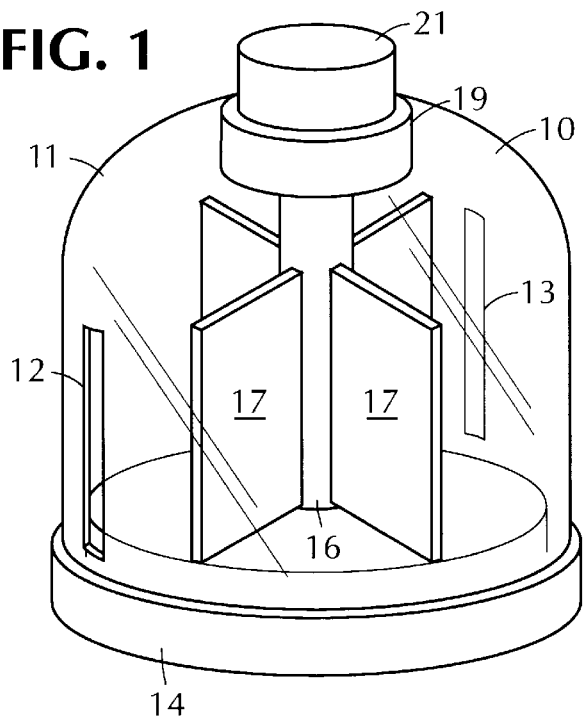
FIG. 1 is a perspective view of a button-actuated air freshener in accordance with the invention.
Figure 2:
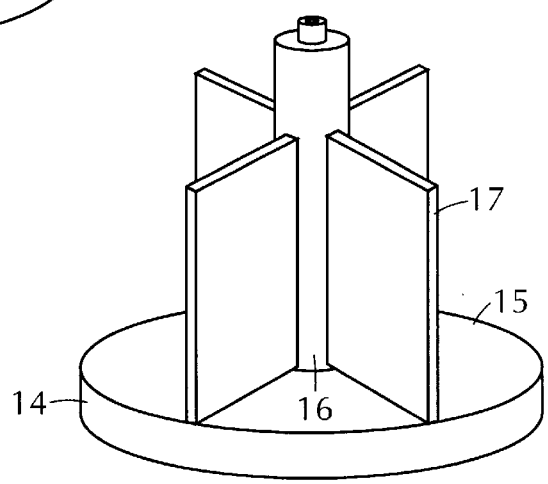
FIG. 2 shows the air freshener with its dome removed to expose its rotatable turret.
Figure 3:
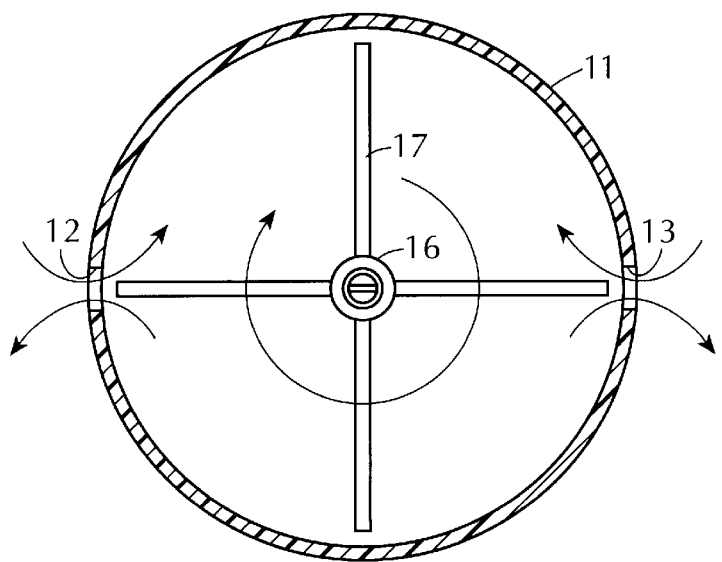
FIG. 3 is a transverse section taken through the rotatable turret.

As shown in FIGS. 1 to 3, an air freshener in accordance with the invention includes a dome 10 having a cylindrical shell 11 provided with diametrically-opposed longitudinal slots 12 and 13 each forming an air vent. Shell 11 is fitted onto a circular base 14. Dome 10 is molded of transparent synthetic plastic material, such as polypropylene or polyethylene.

Rotatable within dome 10 is a turret having a turntable 15 on whose center is anchored a hollow vertical shaft 16 coaxial with the longitudinal axis of shell 11. Radiating from shaft 16 is an array of four wings 17 which are ninety degree apart from each other so that the turret resembles a revolving door.

Each wing 17 is formed by a rigid rectangular panel of porous material, such as open-cell, foam plastic urethane or paper board. The porous panel is impregnated with a fragrance oil having air freshening characteristics which render it capable of masking unpleasant odors in the atmosphere of the enclosure in which the freshener is installed. Thus a pine scent is appropriate to a kitchen, whereas in a living room, a flower bouquet is more desirable.

Figure 4:
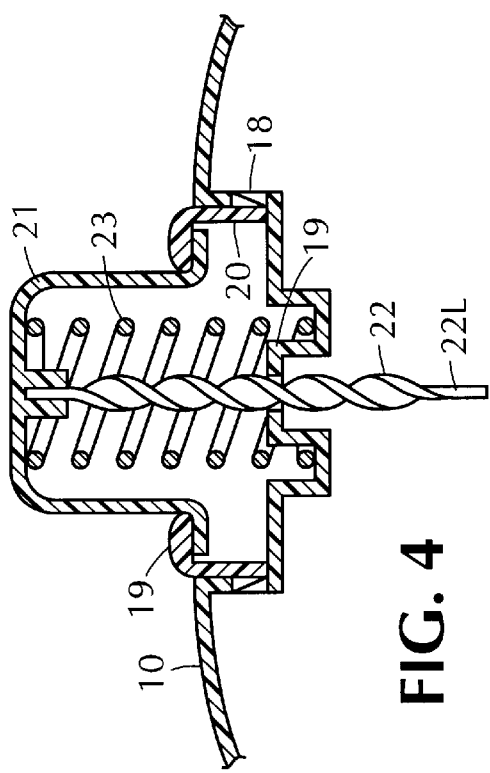
FIG. 4 separately illustrates the actuator-button assembly of the air freshener.

As best seen in FIG. 4, dome 10 is formed with a circular well 18 centered on the top of the dome and is provided with a re-entrant coaxial sleeve 19. Supported in well 18 is an actuator button assembly which includes a plastic collar 20 nested in well 18 and concentric with sleeve 19. Telescoping into collar 20 is a cylindrical actuator button 21 having attached thereto a metal rod 22 the projects through sleeve 19, and is coaxial therewith.

Disposed within button 21 and surrounding sleeve 19 is a helical metal spring 23. Spring 23 is compressed between the closed end of the button and a ledge at the lower end of sleeve 19 whereby when button 21 is depressed, rod 22 is then axially advanced, and when the button is released, the rod is retracted.

Figure 6:
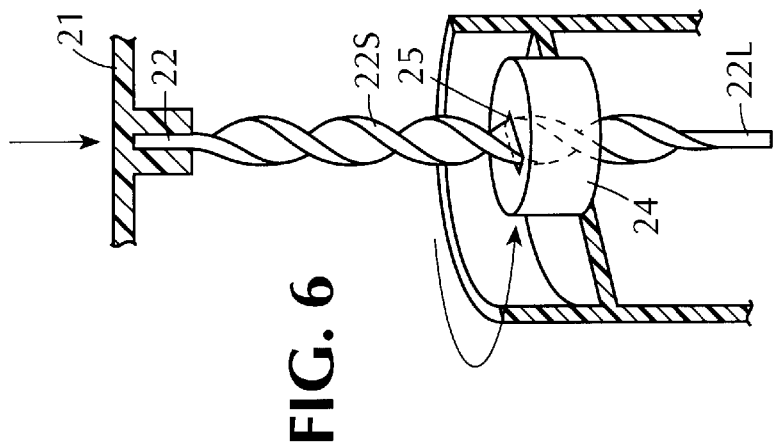
FIG. 6 shows the relationship between the spiral twist rod projecting from the actuator button and the coupling tube at the upper end of the turret shaft.
Figure 5:
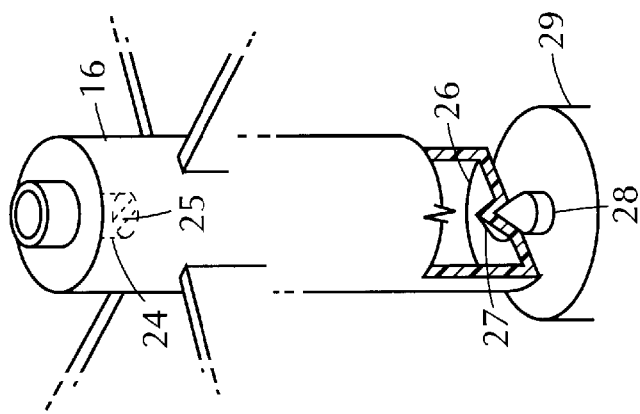
FIG. 5 illustrates the manner in which the shaft of the turret is supported for rotation on the base of the air freshener.

Held within the upper end of hollow shaft 16 is a short tube 24 which as shown in FIG. 5 has a membrane therein provided with a rectangular slot 25. As best seen in FIG. 6, rod 22 is provided with a shank 22S having a spiral twist formation, the tip end of the shank being in the form of a lug 22L having a rectangular crossection. The dimensions of lug 22L match these of slot 25 in the tube at the upper end of the shaft, so that the leg can enter this slot.

The air freshener is assembled by fitting dome 10 over base 10 whereby leg 22L of rod 22 then enters slot 25 in tube 24 at the upper end of shaft 16, and wings 17 of the turret are then within shell 11, thereby operatively coupling the actuator button 21 to the turret.

When button 21 is depressed by an operator, rod 22 is then axially advanced, as shown by the arrow in FIG. 6, and the spiral twist on shank 22S of the rod as the rod is advanced, causes slot 25 in tube 24 to ride up the spiral path to rotate the turret. By repeatedly depressing button 21, the turret may be caused to spin at relatively high speed.

As shown in FIG. 5, inserted in the lower end of hollow shaft 16 anchored at the center of turntable 15 is a closure disc 26 at whose center is a bearing cup 27. Socketed in bearing cup 27 is a bearing pin 28 projecting above a pedestal 29 placed at the center of circular base 14. Thus the turret turntable 15 is supported for rotation on base 14, and as the turret rotates, wings 17 above the turntable sweep the air within the cylindrical shell 11 of the dome.

Operation of Air Freshener

When the air freshener is actuated by depressing button 21 to cause the turret within the dome to spin and to cause wings 17 radiating from the shaft 16 to sweep the air within the dome, this action creates a positive pressure within the dome in the direction of rotation and a negative pressure in the opposite direction.

As a consequence, when each wing 17 of the turret approaches a vent slot 12 and 13, the resultant positive pressure causes air in advance of the wing to be discharged from the vent. But as the wing travels past the same vent, the resultant negative pressure draws atmospheric air into the dome through the vent.

Thus as the turret spins within the dome, air is cyclically sucked into and expelled form the dome. This produce a vortex within the dome, causing air to flow at high velocity across the surfaces of the wings impregnated with fragrance oil. This flow acts to stir the oil within the wings and to bring the oil to the surfaces of the wings and to volatilize the oil at these surfaces to produce an aromatic vapor. This aromatic vapor is intermingled with the air within the dome and is discharged through the vents in the dome into the atmosphere of the enclosure in which the air freshener is installed.

The volume of aromatic vapor that is generated and the rate at which it is discharged into the atmosphere to mask unpleasant odors permeating this atmosphere is controllable by the operator and depends on how vigorously the actuator button is depressed and on how often.

An air freshener in accordance with the invention may be manufactured in a scale appropriate to its intended use. Hence it may be made in a miniature version for installation in an automobile interior, and in a much larger version for a residential chamber. The number of times the button is repeatedly actuated depends on how much vapor is necessary to suffuse the atmosphere of the enclosure with an aromatic vapor.

In practice, the air freshener turntable 15 whose periphery is visible through the transparent shell 11 may be provided with a decorative multi-colored spiral to indicate how fast the turret is spinning. Wings 17 may also be made in different colors to enhance the decorative display produced by the spinning action.

While there has been shown and described a preferred embodiment of a button-actuated air freshener in accordance with the invention, it will be appreciated that many changes and modifications may be made therein without, however, departing from the essential spirit thereof. Thus instead of a mechanism using a spiral twist rod to cause the turret to spin when the button is depressed, a rack and pinion mechanism may be used for the same purpose.

I claim:

1. A button actuated air freshener comprising:
   A. a dome provided with a cylindrical shell having at least one vent mounted on a base;
   B. a turret rotatable within the dome having a vertical shaft coaxial with the shell, and an array of wings radiating from the shaft, each formed of a panel of porous material impregnated with a fragrance oil; and
   C. a spring-biased button mounted on top of the dome operatively coupled to the shaft of the turret whereby each time the button is depressed, this action causes the turret to spin within the dome to create an air vortex therein that acts to volatilize fragrance oil on surfaces of the wings to produce an aromatic vapor that is discharged through said vent in the shell into the atmosphere of an enclosure in which the air freshener is installed to mask unpleasant odors in this atmosphere, whereby repeated depression of the button causes the turret to rotate at high speed to increase the production of aromatic vapor.

2. An air freshener as set forth in claim 1, in which the dome is molded of transparent plastic material.

3. An air freshener as set forth in claim 1, in which each panel is formed of open-cell foam plastic material.

4. An air freshener as set forth in claim 1, in which said array of wings is comprised of four wings ninety degrees apart from each other to simulate a revolving door.

5. An air freshener as set forth in claim 4, in which the wings are supported on a turntable which turns on a bearing within the base.

6. An air freshener as set forth in claim 1, in which said shell is provided by a pair of diametrically-opposed longitudinal slots defining vents.

7. An air freshener as set forth in claim 1, in which said dome is provided with a central well in which is nested a collar, and said button has a cylindrical form that telescopes into said collar.

8. An air freshener as set forth in claim 7, in which said well has a re-entrant, coaxial sleeve, and surrounding said sleeve is a helical spring that is compressed between an upper end of said button and a lower end of said sleeve.

9. An air freshener as set forth in claim 8, in which a rod attached to said upper end of said button projects through said sleeve and is advanced axially when the button is depressed, said rod having a spiral twist shank and a lug at the free end of the shank having a rectangular cross section.

10. An air freshener as set forth in claim 9, in which held in the upper end of said shaft is a tube having a membrane therein provided with a rectangular slot which receives the lug of the rod whereby when the button is actuated to advance the rod, the tube then rides up the spiral twist to rotate the turret.

\* \* \* \* \*